United States Patent [19]

Collier et al.

[11] Patent Number: 5,403,386

[45] Date of Patent: Apr. 4, 1995

[54] CONCENTRATOR APPARATUS FOR DETECTING TRACE ORGANIC COMPONENTS IN AQUEOUS SAMPLES

[75] Inventors: Ledelle Collier, North Wales; Wayne A. Thompson, Jr., Quakertown, both of Pa.

[73] Assignee: Rohm and Haas Company, Philadelphia, Pa.

[21] Appl. No.: 136,504

[22] Filed: Oct. 14, 1993

[51] Int. Cl.6 .............................................. B01D 15/08
[52] U.S. Cl. .................................. 96/105; 96/102; 96/104; 210/198.2; 210/656; 210/659
[58] Field of Search ............................ 73/23.35, 23.41; 96/101, 102, 105, 104; 95/82, 87; 422/89; 210/656, 659, 198.2

[56] References Cited

U.S. PATENT DOCUMENTS

| | | | |
|---|---|---|---|
| 4,500,432 | 2/1985 | Poole | 210/659 |
| 4,701,306 | 10/1987 | Lawrence | 422/101 |
| 5,240,472 | 8/1993 | Sircar | 95/120 |
| 5,250,093 | 10/1993 | Jiang | 96/105 |

OTHER PUBLICATIONS

CDS330 GC Sample Concentrator, Chemical Data Systems, Inc. technical bulletin CO287 1985, pp. 1–8.

*Primary Examiner*—Ernest G. Therkorn
*Attorney, Agent, or Firm*—Michael B. Fein

[57] ABSTRACT

An improvement to a sample concentrator apparatus for extracting and concentrating trace organic components from an aqueous sample for subsequent analysis; and a method for concentrating trace organics.

6 Claims, 2 Drawing Sheets

CONCENTRATOR APPARATUS FOR DETECTING TRACE ORGANIC COMPONENTS IN AQUEOUS SAMPLES

BACKGROUND OF THE INVENTION

1. FIELD OF THE INVENTION

This invention relates to chemical analytical equipment and methods of analysis. More particularly, this invention relates to apparatus and methods used to concentrate trace organic materials from aqueous samples for subsequent analysis.

2. DESCRIPTION OF THE PRIOR ART

U.S. Pat. No. 4,500,432 to Poole et al of Hewlett-Packard Company describes an automated sample concentrator for trace components involves passing a liquid solvent through a first trapping means to absorb the solutes then flushing the first trapping means with supper critical fluid and reducing its solubility parameter in a second trapping means so as to absorb the desired solutes in said second trapping means.

U.S. Pat. No. 4,701,306 to Lawrence et al describes a method for sampling and detecting trace quantities of amine vapors in ambient atmospheres by collecting them in a concentrator having two adsorber components, one a polymeric adsorbent for amines and the other a selected alkaline adsorbent.

Chemical Data Systems Inc., Oxford, Pa., in a 1985 bulletin identified as CO287, describes the CDS 330 GC sample concentrator. In particular, the CDS 330 concentrator module has sample inlet, injection ports for direct injection into the internal trap or GC, an internal trap, a GC transfer line, an external cryogenic trap, a sparge vessel, a thermal desorber, carrier gas flow control, and pressure control. The bulletin illustrates the "purge and trap" of liquids and slurries method in which liquid samples in the sparger vessel are continuously purged with sparge (carrier) gas during the programmed period. Volatile organic components (V) are thus extracted and transferred to the trap where they are adsorbed and concentrated. When the purge period is complete and the 330 has received the GC ready signal, the trap is automatically backflushed and pulse-heated to desorb the trapped volatiles to the GC for analysis. Enhanced purge and trap is accomplished by using the optional heated sparger vessel to increase the vapor pressure of sample components and thus improve recovery of volatile organics. The 330's optional impinger vessel accessory makes it possible to extract and concentrate volatile organics from sludges and slurries that contain as much as 20 percent solids.

I have discovered a problem with the purge and trap method due to the wetness of the gas which is passed through the trap.

SUMMARY OF THE INVENTION

I have discovered that a sample concentrator apparatus similar to the CDS 330 can be improved by providing a dryer packed with cellulose fibers between the sparger and the trap.

More particularly, my improvement comprises such a dryer, means for directing sparge gas containing extracted organic components from the sparger vessel to the dryer in a first direction for drying, means for directing the resultant dried sparge gas containing the extracted organic components from the dryer to the trap, and means for directing dried gas in the reverse direction of the first direction through the dryer so as to remove collected water from the dryer and thereby regenerate the dryer.

In another aspect the invention comprises the method of concentrating trace organics from an aqueous sample for analysis by gas chromatography comprising passing a sparge gas through the sample in a sparger vessel so as to extract trace organics, the improvement comprising directing the flow of the extract during a drying period through dryer having cellulose fiber drying material and directing dry gas through the dryer during a regeneration period to as to remove water and regenerate the dryer.

DETAILED DESCRIPTION AND THE PREFERRED EMBODIMENTS

Sample concentrator apparatus for extracting and concentrating trace organic components from an aqueous sample for subsequent analysis. Such apparatus comprise a sparger vessel for holding said aqueous sample, means for passing sparge gas through said aqueous sample in said sparger vessel to extract said organic components from said aqueous sample, a trap for adsorbing and concentrating the extracted organic components, means for directing the sparge gas containing the extracted organic components from said sparger vessel to said trap, means for backflushing and heating said trap to desorb the resultant concentrated extracted organic components, and means for injecting said concentrated extracted organic components into an analytical instrument for analysis. The subsequent analysis is by gas or liquid chromatography, infrared, or the like.

An example of such apparatus is the aforementioned CDS330 of Chemical Data Systems, Inc., Oxford, Pa.

The improvement of the present invention comprises a dryer packed with cellulose fibers, and means for directing the sparge gas from the sparger vessel to the dryer in a first direction for drying, and means for directing the resultant dried sparge gas from the dryer to a trap. During the drying period the method of the invention includes passing the sparge gas through the sample in the sparger vessel so as to extract the trace organics and directing the flow of the extract during a drying period through a dryer having cellulose fiber drying material. The improved apparatus also includes a method for directing dry gas in the reverse direction of the first direction through the dryer so as to remove collected water from the dryer and thereby regenerate the dryer. According to the method of the invention, this reversal of direction is performed during a regeneration period so as to remove water and regenerate the dryer.

Figure 1:
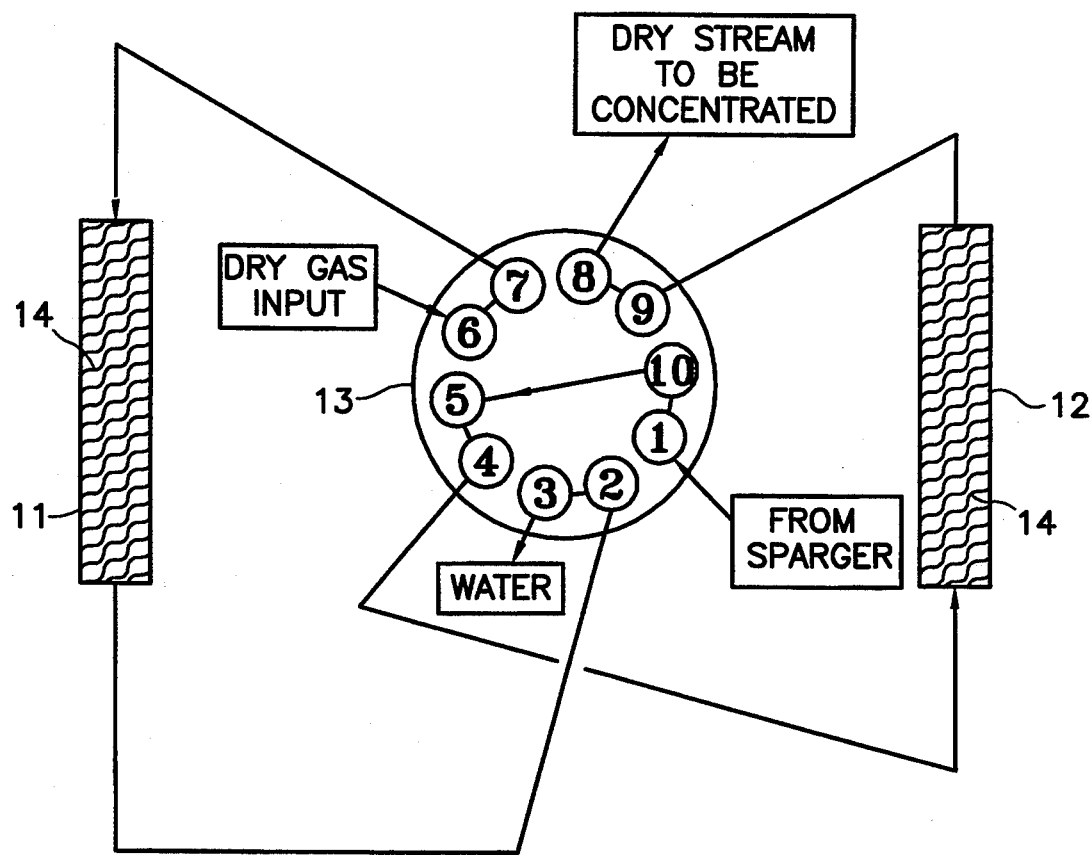
FIG. 1 is a schematic diagram of the flow path through a ten port valve in a first position, in a two-dryer configuration, with dryer 12 being operated to dry the flow of gas from the sparger to the concentrator while dryer 11 is being regenerated.
Figure 2:
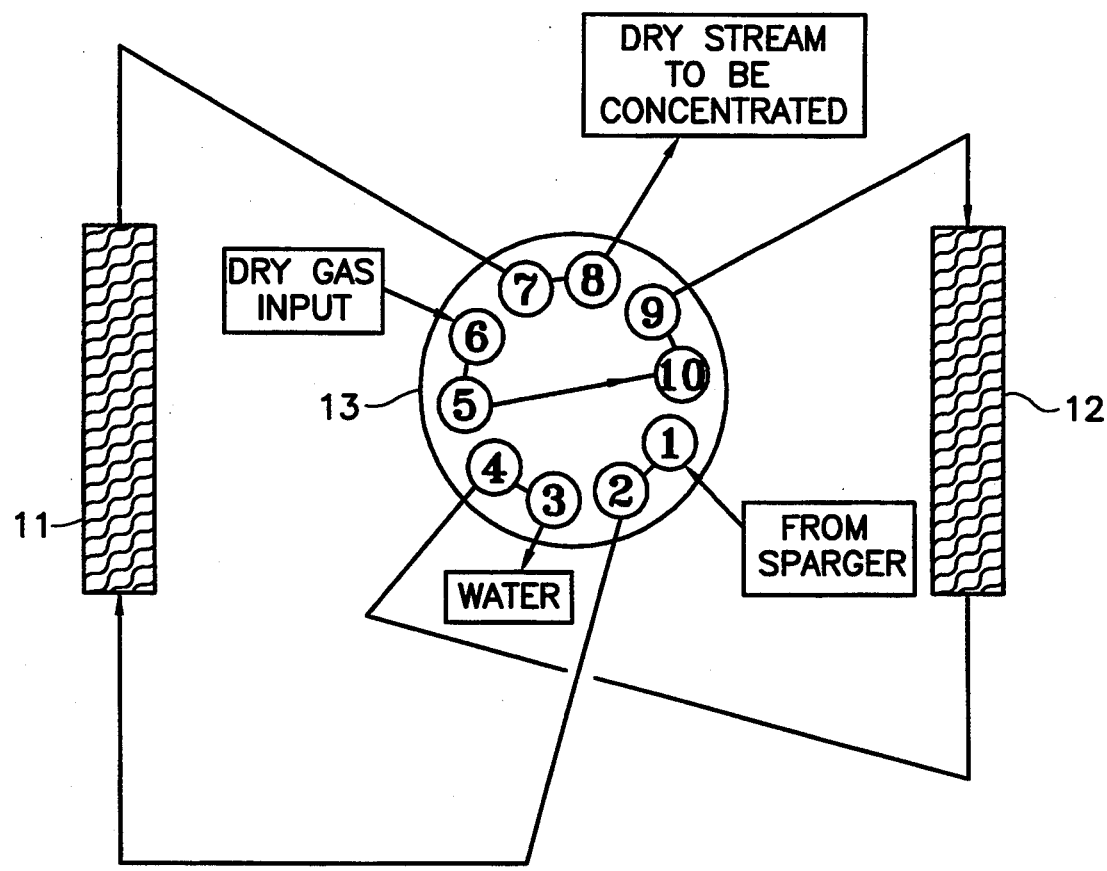
FIG. 2 is a similar schematic of the flow paths of a two dryer configuration showing dryer 11 being utilized to dry the stream of gas from the sparger prior to introduction to the concentrator while dryer 12 is being regenerated.

A preferred embodiment of the invention has two dryers, although more than two dryers could also be used. In the preferred embodiment, means are provided for directing the sparge gas containing the extracted components through one dryer at a time, while directing dry gas through the other dryer so as to regenerate it. In the preferred embodiment, such directing means include a switching valve adapted to direct the flow of at least two streams simultaneously. One such suitable valve is a ten port switching value manufactured by Carle Manufacturing Company, Model No. 0421 and schematic thereof is illustrated in FIGS. 1 and 2 as 13. The dryer itself may be any metal, plastic or glass vessel having two ports to which may be connected lines so that no leaks are present. The cellulose material is preferably rayon. We have found that rayon is extremely efficient and may be used for many cycles before it needs to be replaced.

The analytical instruments used are gas or liquid chromatographs, infrared detectors, and the like.

Referring now to FIG. 1, the schematic illustrates dryer 11 being regenerated while dry 12 is being operated to dry the flow of gas from the sparger. According to FIG. 1, the gas containing organic components for analysis enters at port 1 and is directed through the valve out port 4 to the bottom of dryer 12 containing cellulose fibers 14 and then out the top of dryer 12 into switching valve port 9, out port 8 to the concentrator trap. Simultaneously, dry gas input enters valve 13 at 6, exits at 7 to the top of dryer 11 where it is passed through the wet cellulose 14 so as to remove the water which exits dryer 11 at the bottom. The wet gas is passed to switching valve port 2 and out port 3 to waste.

FIG. 2 shows the switching valve switched to the opposing position which causes reversal of direction of flow through the two dryers. More specifically, the gas from the sparger containing trace organic components enters at port I but now is switched to port 2 where it exits and is directed to the bottom of dryer 11 through which it is dried and exits at the top and is directed to switching valve port 7, out port 8 to the concentrator trap. Simultaneously, dryer 12 is being regenerated with dry gas which again is inputted at port 6 but is switched to port 9 where it exits and is directed to the top of dryer 12 for drying and returned from the bottom of dryer 12 back to port 4 and out port 3 to the waste stream.

I have found that the reliability of the gas chromatograph/mass spectrophotometer analysis of samples containing trace organic components dissolved in water by the purge and trap method is greatly improved by the apparatus and method of the present invention. The reliability is very important is certain chemical analytical methods, especially in the environmental and agricultural area where such methods are used m detect impurities in drinking water and the like.

While this invention has been described and illustrated in great detail herein, various alternative modifications and improvements should be become apparent to those skilled in the art without departing from the spirit and scope of the invention.

What is claimed is:

1. In a sample concentrator apparatus for extracting and concentrating trace organic components from an aqueous sample for subsequent analysis by gas chromatography, said apparatus comprising
    a sparger vessel for holding said aqueous sample,
    means for passing sparge gas through said aqueous sample in said sparger vessel to extract said organic components from said aqueous sample,
    a trap for adsorbing and concentrating the extracted organic components,
    means for directing the sparge gas containing the extracted organic components from said sparger vessel to said trap,
    means for backflushing and heating said trap to desorb the resultant concentrated extracted organic components,
    means for injecting said concentrated extracted organic components into an analytical instrument for analysis;
    the improvement comprising:
    a dryer packed with cellulose fibers,
    means for directing said sparge gas containing said extracted organic components from said sparger vessel to said dryer in a first direction for drying,
    means for directing the resultant dried sparge gas containing said extracted organic components from said dryer to said trap,
    means for directing dry gas in the reverse direction of said first direction through said dryer so as to remove collected water from said dryer and thereby regenerate said dryer.

2. Apparatus according to claim 1 having at least two dryers and means for directing said sparge gas containing said extracted components through one dryer at a time while directing dry gas through another dryer.

3. Apparatus according to claim 2 wherein said means for directing said sparge gas through one dryer at a time is a switching valve adapted to direct the flow of at least two gas streams simultaneously.

4. Apparatus according to claim 2 having two dryers.

5. Apparatus according to claim 1 wherein said cellulose is rayon.

6. Apparatus according to claim 1 wherein said analytical instrument is a gas chromatograph, liquid chromatograph, or infrared detector.

* * * * *